(12) United States Patent
Nagasaka (10) Patent No.: US 9,370,441 B2
(45) Date of Patent: Jun. 21, 2016

(54) INTRAOCULAR LENS INJECTION INSTRUMENT

(71) Applicant: NIDEK CO., LTD., Gamagori-shi, Aichi (JP)

(72) Inventor: Shinji Nagasaka, Okazaki (JP)

(73) Assignee: NIDEK CO., LTD., Gamagori-shi (JP)

( * ) Notice: Subject to any disclaimer, the term of this patent is extended or adjusted under 35 U.S.C. 154(b) by 750 days.

(21) Appl. No.: 13/631,001

(22) Filed: Sep. 28, 2012

(65) Prior Publication Data

US 2013/0085507 A1    Apr. 4, 2013

(30) Foreign Application Priority Data

Sep. 30, 2011   (JP) ................................. 2011-215938
Aug. 10, 2012   (JP) ................................. 2012-177818

(51) Int. Cl.
*A61F 9/00*   (2006.01)
*A61F 2/16*   (2006.01)

(52) U.S. Cl.
CPC ............. *A61F 9/0017* (2013.01); *A61F 2/1678* (2013.01)

(58) Field of Classification Search
CPC ... A61F 2/1662; A61F 2/1664; A61F 2/1667; A61F 2/167; A61F 2/1672; A61F 2/1675; A61F 2/1678; A61F 9/0017
See application file for complete search history.

(56) References Cited

U.S. PATENT DOCUMENTS

| 6,228,094 | B1 | 5/2001 | Erdman |
| 6,607,537 | B1 | 8/2003 | Binder |
| 2001/0007942 | A1 | 7/2001 | Kikuchi et al. |
| 2003/0181921 | A1 | 9/2003 | Jeannin et al. |
| 2003/0212406 | A1 | 11/2003 | Kobayashi et al. |
| 2007/0150055 | A1* | 6/2007 | Pynson ........................ 623/6.12 |
| 2011/0046635 | A1 | 2/2011 | Pankin et al. |

FOREIGN PATENT DOCUMENTS

EP    2 255 751 A1    12/2010
JP    A-2001-104347   4/2001

OTHER PUBLICATIONS

Extended European Search Report issued in European Application No. 12186462.3 dated May 7, 2013.

* cited by examiner

*Primary Examiner* — Thomas McEvoy
(74) *Attorney, Agent, or Firm* — Oliff PLC (57) ABSTRACT

An intraocular lens injection instrument including: an injection part formed with an inner wall for folding the soft IOL and a front end for injecting the IOL folded along the inner wall into an eye; a cylinder body part provided with the injection part at its end portion; a push member for pushing the IOL toward the front end of the injection part, a restriction member attached to the cylinder body part to restrict movement of the IOL which is placed outside the axis; and a release member for releasing the restriction member and pushing the IOL onto the axis, wherein the release member includes a contact portion to be brought into contact with the IOL when the restriction by the restriction member is released, the contact portion having a setting surface to be brought into contact with the IOL placed on the axis.

5 Claims, 7 Drawing Sheets

INTRAOCULAR LENS INJECTION INSTRUMENT

This application is based upon and claims the benefit of priority from the prior Japanese Patent applications No. 2011-215938, filed Sep. 30, 2011; and No. 2012-177818, filed Aug. 10, 2012, the entire contents of which are incorporated herein by reference.

FIELD OF THE INVENTION

The present invention relates to an intraocular lens injection instrument for injecting an intraocular lens into an eye.

RELATED ART

It has been known an intraocular lens injection instrument (injector) that stores and conveys an intraocular lens (IOL) in the injector without applying stress to the foldable IOL. In use, a holding member holding the IOL in position is detached. Then, the IOL released from holding or retention state is pushed by a push member called a plunger. Thereby, the IOL folded into a tiny piece in the injector is injected from a front end of the injector. To be specific, the IOL is stored outside an axis of an injector body. Then, in use, the IOL is pushed onto the axis by a predetermined component to release the holding state of the IOL (JP2001-104347A).

SUMMARY OF INVENTION

Problems to be Solved by the Invention

However, there is a case that the IOL is not properly positioned on the axis of the injector when the IOL is pushed onto the axis from the outside of the axis to release the holding state. For instance, there are cases that the IOL could be bent and that the IOL could be inclined relative to the axis when the IOL is pushed onto the axis from the outside of the axis. Due to such cases, if there is created an unintended gap between an inner wall of the injector and the IOL, the tip end of the plunger could slip under an undersurface of an optical part of the IOL or run onto the optical part when the IOL is pushed toward the front end of the injector by the plunger, which could cause scratches on the optical part.

For example, in JP2001-104347A, the IOL is pushed by a push member to be deformed so that the IOL is moved onto the axis from the outside of the axis. In this case, if the push member is pushed slowly, an unintended gap is apt to be created between the IOL and the inner wall of the injector. On the other hand, if the push member is pushed forcibly, the IOL could be damaged when deformed.

The present invention has been made to solve the above problems and has a purpose to provide an intraocular lens injection instrument capable of appropriately shifting the IOL from a storage state to a use state.

The present invention can provide an intraocular lens injection instrument capable of appropriately shifting the IOL from a storage state to a use state.

Means of Solving the Problems

To solve the above problem, one aspect of the present invention is an intraocular lens injection instrument for injecting an intraocular lens (IOL) into a patient's eye, including: an injection part formed with an inner wall for folding the soft IOL and a front end for injecting the IOL folded along the inner wall into an eye; a cylinder body part provided with the injection part at its end portion; a push member for pushing the IOL toward the front end of the injection part, the push member being movable back and forth along an axis extending from the front end of the injection part to a rear end of the intraocular lens injection instrument; a restriction member attached to the cylinder body part to restrict movement of the IOL which is placed outside the axis; and a release member for releasing restriction of the movement of the IOL restricted by the restriction member and pushing the IOL onto the axis, wherein the release member includes a contact portion to be brought into contact with the IOL when the restriction by the restriction member is released, the contact portion having a setting surface to be brought into contact with the IOL placed on the axis.

Another aspect of the present invention is an intraocular lens injection instrument for injecting an intraocular lens (IOL) into a patient's eye, including: an injection part formed with an inner wall for folding the soft IOL and a front end for injecting the IOL folded along the inner wall into an eye; a cylinder body part provided with the injection part at its end portion; a push member for pushing the IOL toward the front end of the injection part, the push member being movable back and forth along an axis extending from the front end of the injection part to a rear end of the intraocular lens injection instrument; and a storage member attached obliquely to the cylinder body part, the storage member including a restriction member to restrict movement of the IOL placed outside the axis and a release member to release restriction of the movement of the IOL restricted by the restriction member and push the IOL onto the axis, wherein the restriction of the IOL by the restriction member is released by the release member by a rotation operation of the storage member rotating about the cylinder body part.

DESCRIPTION OF EMBODIMENTS

Figure 1:
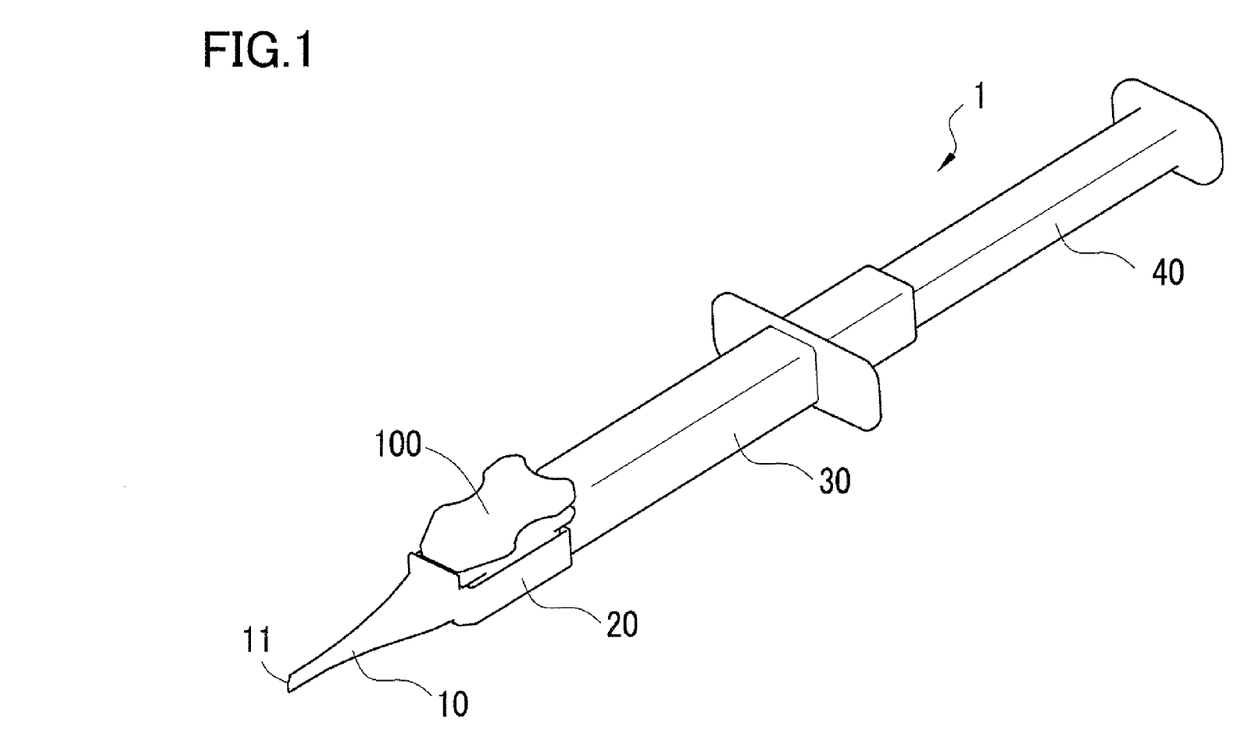
FIG. 1 is an external schematic view of an intraocular lens injection instrument (injector)
Figure 2A:
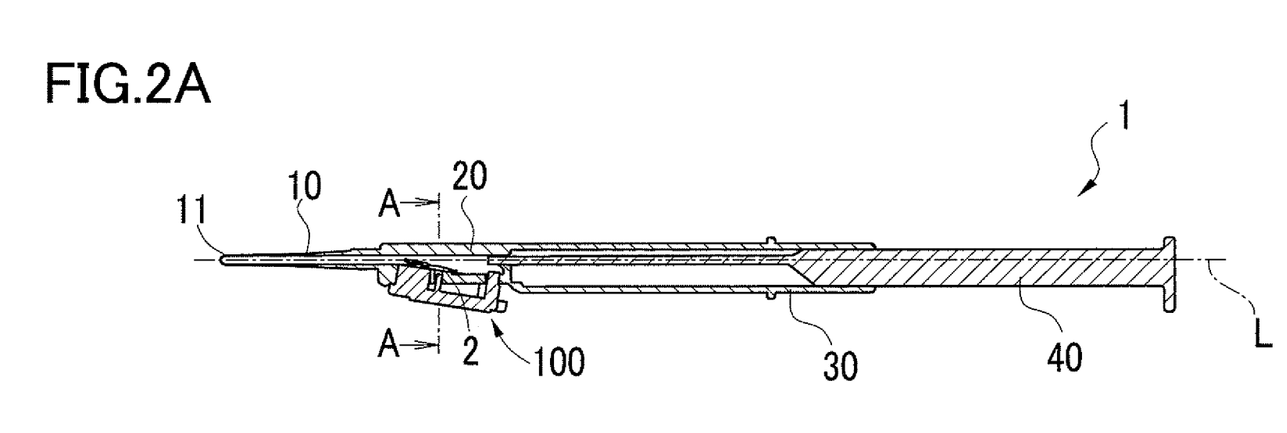
FIG. 2A is a sectional diagram of the injector during storage.
Figure 2B:
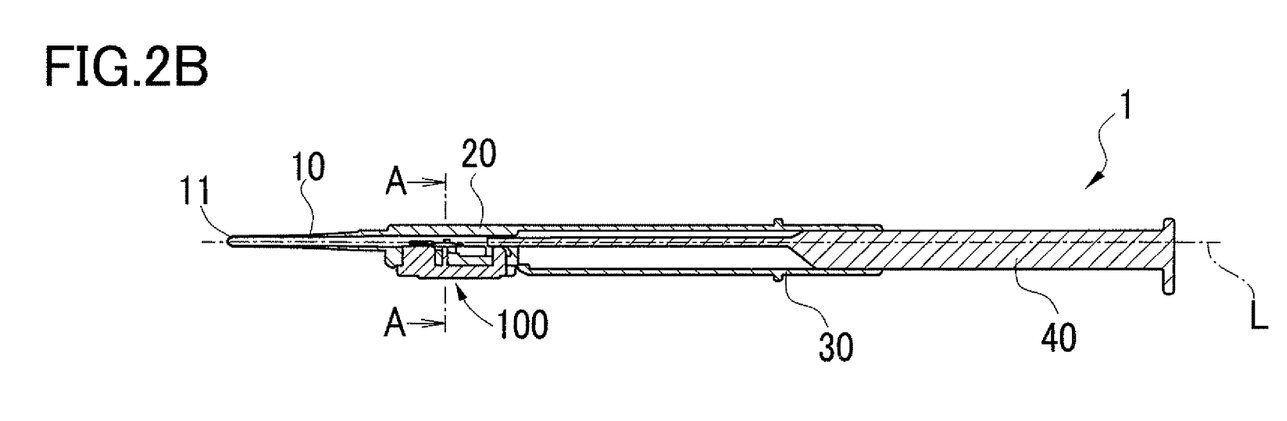
FIG. 2B is a sectional diagram of the injector during release.
Figure 3:
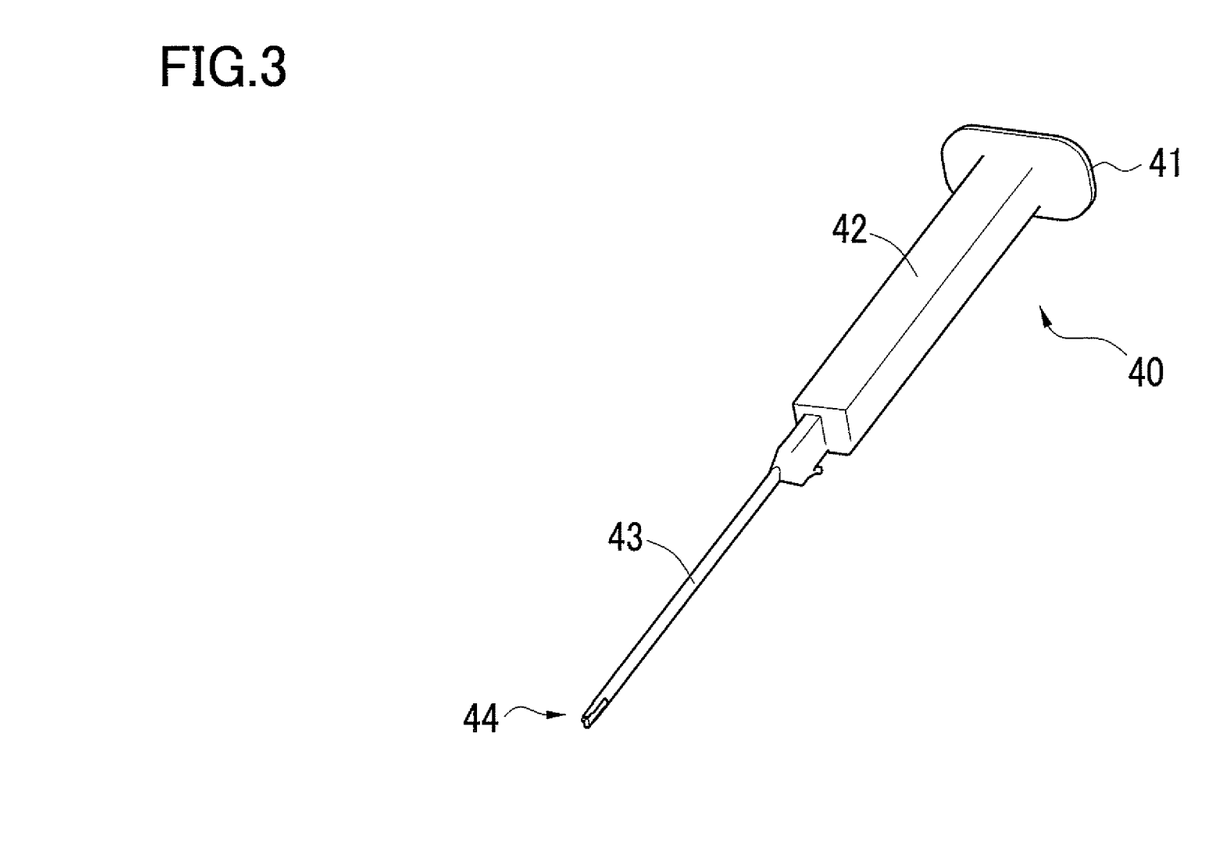
FIG. 3 is an explanatory view of a configuration of a plunger.
Figure 4:
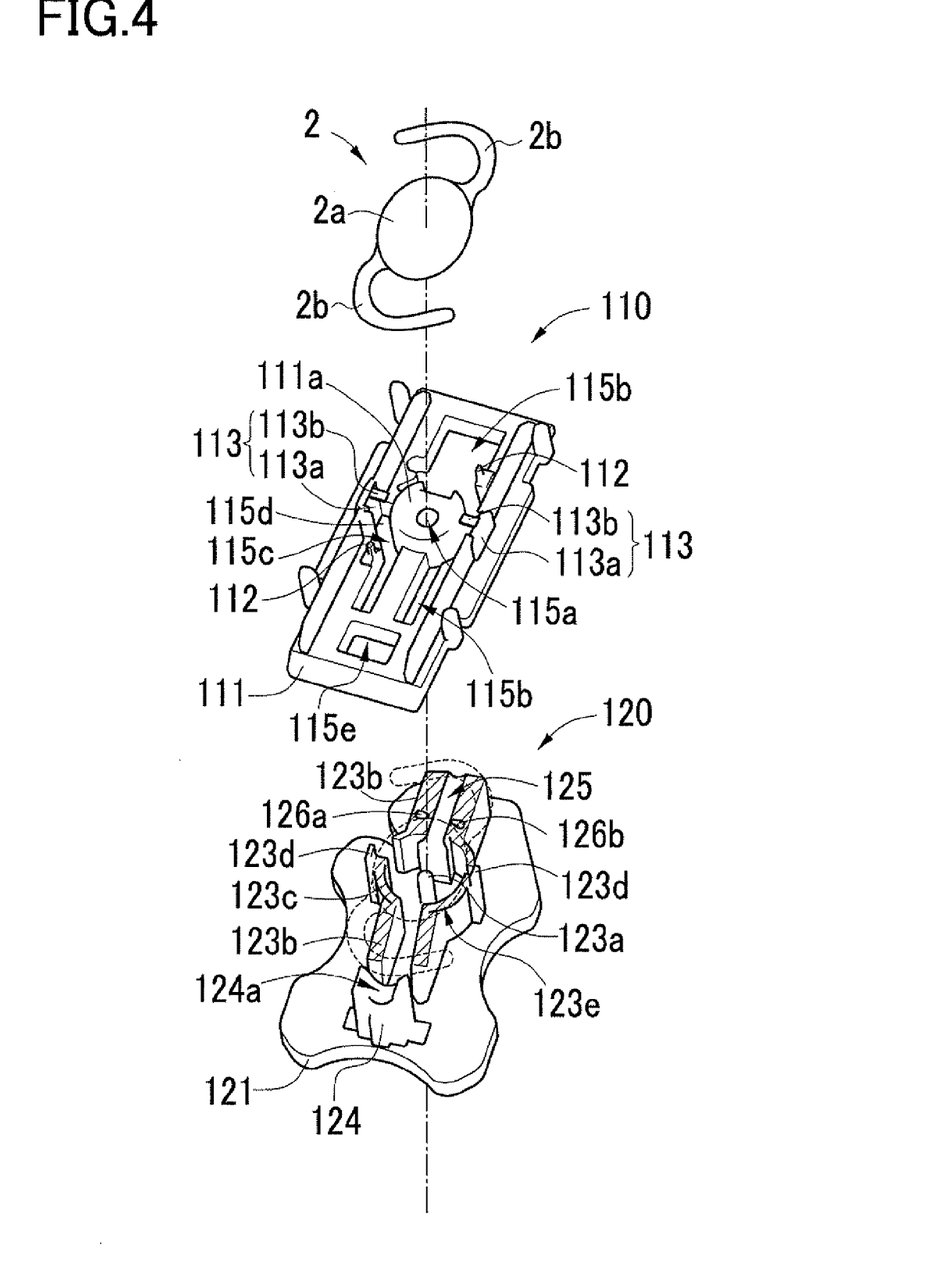
FIG. 4 is an explanatory view of a storage part for storing an intraocular lens (IOL)

Detailed description of the present invention will be now explained with reference to the accompanying drawings. FIG. 1 is an external schematic view of an intraocular lens injection instrument (hereinafter, referred to as an injector) 1. FIGS. 2A and 2B are sectional side views of the injector 1 taken along an axis. FIG. 2A is a sectional view when an intraocular lens (IOL) is stored, and FIG. 2B is a sectional view when the IOL is released from restriction into a use state. In the present disclosure, a straight line extending from a front end 11 of an injection part 10 to a rear end of a plunger 40 is defined as an axis L. FIG. 3 is an explanatory view of a configuration of the plunger 40. FIG. 4 is an explanatory view of an IOL storage part 100.

The injector 1 includes a cylinder body part (hereinafter, referred to as a body) 30, a push member (hereinafter, referred to as a plunger) 40, the IOL storage part (hereinafter, referred to as a storage part) 100. The body 30 includes the injection part 10 and a setting part 20. The injector 1 is formed of a resin material and the like by molding. For example, the body 30 and the storage part 100 are separately molded and after that, they are connected at not shown connecting points. Alternatively, the injector 1 may be formed by cutting process by shaving a resin material.

In the present disclosure, an IOL 2 stored in the storage part 100 is a one-piece IOL in which an optical part 2a and a pair of support parts 2b made of soft material are integrally formed (see FIG. 4). Other than this, the IOL 2 may be the known one which is foldable by use of the injector 1. For example, a three-piece IOL in which an optical part and a pair of support parts are separately formed, a plate-type IOL, and others may be adopted.

The injection part 10 of the body 30 is of a hollow cylindrical shape. Further, the injection part 10 has a region (inner wall shape) where an inner diameter of a passage is gradually narrow (tapered) toward the front end 11. The front end 11 is formed with a cutout (bevel) for injecting the IOL 2 outside. While passing through the injection part 10, the IOL 2 is folded into a tiny piece along the inner wall of the injection part 10 and then injected out of the front end 11.

The setting part 20 is provided on a rear end of the injection part 10 to form a space (clearance) for placing the IOL 2 in use state. The setting part 20 includes a setting surface on which the IOL 2 in use state is to be placed. The storage part 100 stored inside with the IOL 2 and an opening (omitted with its reference sign in the figure) of the setting part 20 close together to store the IOL 2 inside the injector 1.

The storage part 100 serves as a lid member to close the opening of the setting part 20. Further, the storage part 100 serves as a restriction member to restrict movement of the IOL 2 without applying stress to the IOL 2 placed outside the axis L during storage and conveyance of the injector 1. The storage part 100 also serves as a release member to release retention of the IOL 2 placed outside the axis L and to bring the IOL 2 onto the axis L during use of the injector 1. Detailed explanation of the storage part 100 will be given later.

In the present embodiment, the IOL 2 is regarded as being outside the axis L when a peripheral edge (edge) 2c of the optical part 2a is positioned out of contact with the plunger 40 irrespective of back and forth movement of the plunger 40. In addition to this, when the IOL 2 sticking with its adhesion is unstuck by pressing a release member 120 to move the IOL 2 onto the axis L, the IOL 2 is regarded as being outside the axis. For example, even in a case that a part of a tip portion of the plunger 40 comes to contact with the peripheral edge 2c of the optical part 2a by the back and forth movement of the plunger 40, the IOL 2 during storage is regarded as being outside the axis L as long as the IOL 2 is moved onto the axis L by pressing of the release member 120.

The plunger 40 is to fold the IOL 2 into a tiny piece inside the injection part 10 and to push and inject the IOL 2 into an eye from the front end of the injection part 10. As shown in FIG. 3, the plunger 40 includes a press part 41 which an operator presses, a basal part 42 connected to the press part 41, a push rod 43 connected to the basal part 42, and a tip portion 44 connected to a distal end of the push rod 43. The tip portion 44 is to be brought into contact with the optical part 2a to push the IOL 2. The plunger 40 having the above configuration is allowed to move back and forth in a passage extending from the body 30 to a front end of the injection part 10.

Herein, a surface of the tip portion 44 to be placed into contact with the IOL 2 (peripheral edge 2c) is referred to as a contact surface (not shown) of the tip portion 44 and a side surface (not shown) surrounding the contact surface is referred to as a side surface. A protrusion for preventing the tip portion 44 of the plunger 40 from running onto the optical part 2a may be formed on a lower side of the contact surface of the tip portion 44. Further, another protrusion to press the support part 2b may be formed in the contact surface at a position corresponding to a folding point of the support part 2b at a rear side. Thus, the support part 2b is reliably held by the tip portion 44. In addition, a space for holding the optical part 2a may be formed between the above-mentioned two protrusions. A part of the optical part 2a is held in the space, and thereby a pushing operation of the IOL 2 can be conducted more reliably. Furthermore, another protrusion may be provided on an upper side of the contact surface. The protrusion on the upper side is to prevent the support part 2b from being separated from the contact surface when the support part 2b is pushed by the tip portion 44. Also, cutouts may be formed in right and left portions of the side surface of the tip portion 44 so that clearances are created between the tip portion 44 and the inner wall of the injection part 10 to escape a connecting point (root) of the support part 2b at the rear side and the optical part 2a toward a rear side. Thereby, the support part 2b at the rear side is positioned in the clearances, and breakage of the support part 2b is prevented. Further, a slant surface having a predetermined angle slanted from a front end to a rear end may be formed on an underside (a portion to be brought into contact with a centering portion 124 described later during use) of the tip portion 44. When the IOL 2 is folded, the tip portion 44 is temporarily lifted by this slant surface, and thereby a part of the support part 2b at the rear side can be preferably tucked onto the optical part 2a.

Figure 7:
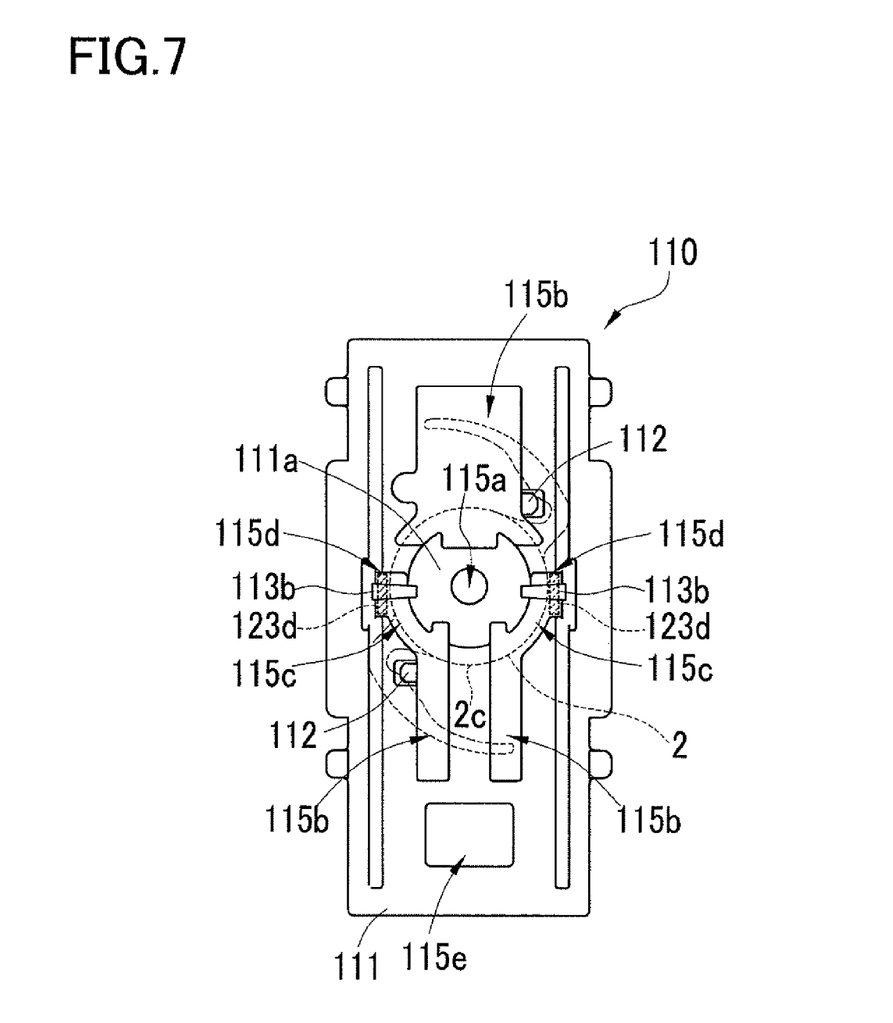
FIG. 7 is a top view of a restriction member and a release member.

Next, the configuration of the storage part 100 is explained in detail. FIG. 4 is a perspective view of the IOL 2 and each component constituting the storage part 100. FIG. 7 is a top view of a restriction member 110 and a release member 120. The storage part 100 consists of a combination of the restriction member 110 and the release member 120. The restriction member 110 is to retain (restrict) the unused IOL 2 without applying stress. The release member 120 is to release restriction of the IOL 2 restricted by the restriction member 110. Incidentally, the state that the IOL 2 is not subjected to stress includes a state that stress is applied to an extent that unintended deformation does not occur when the IOL 2 is stored for a long period.

The restriction member 110 includes a base 111, a stage 111a positioned corresponding to the optical part 2a of the IOL 2, restriction parts 112 and 113 for restricting movement of the IOL 2, through holes 115a to 115e, and others. Each through hole 115a to 115e is formed by boring a part of the base 111 (stage 111a) to allow a part of the release member 120 to pass therethrough. The stage 111a and the restriction parts 112 and 113 have a columnar portion extending from the base 111, respectively.

The base 111 has a size and a shape conforming to an opening of the setting part 20 so as to close the opening. The columnar stage 111a perpendicularly extends from the base 111 toward an inside of the body 30 when the storage part 100 and the setting part 20 are closed. A surface (end portion) of the stage 111a on which the IOL 2 is placed is sloped. Thereby, when the optical part 2a is placed on the stage 111a, the IOL 2 as a whole is placed obliquely with respect to the axis L (placed with a predetermined slant angle). In other words, the support part 2b closer to the front end 11 (at a front side) is placed close to the axis L closer than the support part 2b at the rear side arranged close to the rear end (the plunger 40 side). Then, when the release member 120 is rotated about a not-shown rotation axis at the front end 11 side to come close to the body 30, the whole IOL 2 is successively pushed from the support part 2b at the front side to the support part 2b at the rear side so that the IOL 2 is released from the restriction by the restriction member 110. According to the above configuration, pressing amount of the release member 120 can be reduced, and thus it is advantageous for downsizing the injector 1. Further, the restriction of the IOL 2 is uniformly released by a rotational operation of the release member 120.

The restriction parts 112 and 113 have columnar portions extending perpendicularly from the base 111 to the inside of the body 30 when the storage part 100 and the opening of the setting part 20 are closed. The restriction parts 112 are provided so as to be aligned (be in contact) with an outer circumferential shape (the peripheral edge 2c) of the optical part 2a of the IOL 2. The restriction parts 112 are provided as corresponding to the two connecting points (symmetrical points) of the optical part 2a and the support parts 2b. By the restriction parts 112, the IOL is prevented from moving in a horizontal direction and from rotating about a center of the optical part 2a on the base 111.

The restriction parts 113 are provided outside away form the peripheral edge 2c of the optical part 2a placed on the stage 111a. Herein, the restriction parts 113 are formed on both left and right sides of the optical part 2a. The left and right sides indicate a direction orthogonal to the axis L of the plunger 40. The restriction part 113 includes a columnar portion 113a and an end portion 113b. The columnar portion 113a is a columnar-shaped member extending perpendicular to the base 111. The end portion 113b is a protrusion-like member formed by bending a distal end of the columnar portion 113a toward inside (toward a center of the optical part 2a), and thus extends from the circumference (peripheral edge 2c) of the optical part 2a to the inside by a predetermined distance in the horizontal direction. Specifically, the end portion 113b is supported by the columnar portion 113a. The end portion 113b has a length long enough to restrict movement of the restricted IOL 2 (optical part 2a) toward the pressing direction by the release member 120.

According to the above configuration, the optical part 2a is prevented from moving in the left and right direction (horizontal direction) with respect to the base 111 by the columnar portion 113a. By the end portion 113b, an upper surface of the optical part 2a is supported, so that the IOL 2 is prevented from moving in the pressing direction (perpendicular direction with respect to the axis L) of the release member 120. A clearance is formed between the peripheral edge 2c of the optical part 2a and the restriction parts 113 (columnar portions 113a). In the clearance, a through hole for passing a part of a contact portion (release portion) 123d to be described later is formed. The end portion 113b is lifted by the contact portion 123d having passed the through hole, and thereby the restriction of the IOL 2 can be released without applying load to the IOL 2.

The end portion 113b is not deformed by the weight or movement (slight movement) of the IOL 2. The end portion 113b has a thickness having flexibility and strength to be deformed along the pressing direction of the IOL 2 by the pressing force applied from the release member 120 to the connecting point (bending point) of the columnar portion 113a and the end portion 113b.

Each of the through holes 115a to 115e is formed to pass a part of the release member 120. The through hole 115a is formed in a center (position corresponding to a center of the optical part 2a) of the stage 111a. The through holes 115b are positioned corresponding to a pair of the support parts 2b of the IOL 2 restricted by the restriction member 110. The through hole 115c is formed along the peripheral edge 2c of the optical part 2a. The through holes 115d are formed in the space created by the restriction parts 113 and the peripheral edge 2c of the optical part 2a. The through hole 115e is formed corresponding to the centering portion 124 of the release member 120 which is explained later.

Since the through holes 115a to 115c are formed as corresponding to each part of the IOL 2, the IOL 2 is uniformly (with well-balanced) pushed by the release member 120 having passed the through holes 115a to 115c. Further, parts of the release member 120 pass the through holes 115d formed between the columnar portions 113a and the peripheral edge 2c of the optical part 2a, thereby pushing away up the end portions 113b, allowing the IOL 2 to move onto the axis L. Namely, the restriction by the end portions 113b is released by the release member 120 before the IOL 2 is moved onto the axis L, so that the IOL 2 can be moved onto the axis L without contacting the end portions 113b (without being subjected to unnecessary load).

In the present disclosure, parts of the release member 120 passing through the through holes 115d and the peripheral edge 2c of the optical part 2a come close to an extent that the release member 120 and the optical part 2a do not contact with each other. Therefore, a side wall of the release member 120 that has passed the through holes 115d serves as a guiding portion to restrain inclination (misalignment) of the IOL 2 while guiding movement of the IOL 2 onto the axis L.

The release member 120 includes a pressing portion 121 pressed by an operator, contact portions 123a to 123d coming to contact with the IOL 2, the centering portion 124 for preventing wobbling of the plunger 40. The contact portions 123a to 123d and the centering portion 124 each have a columnar shape extending in a perpendicular direction from a front surface (a side surface facing the restriction member 110) of the pressing portion 121.

The pressing portion 121 of an arbitrary shape has a predetermined area large enough for an operator to press. In the present embodiment, the pressing portion 121 is attached to the injector 1 obliquely from the front end 11 (not shown rotation axis) side to the rear end of the injector 1 such that the inclination of the pressing portion 121 conforms to the inclination of the IOL 2 which is placed obliquely relative to the axis L on the restriction member 110 (stage 111a) (see FIG. 2A). Thereby, the front end 11 side of the release member 120 is positioned closest to the axis L with respect to the body 30, and the distance from the axis L is gradually increased toward the rear end side.

Each contact portion 123a to 123d of columnar shape has a distal end having an almost similar shape to (slightly smaller than) each through hole 115a to 115d so that each contact portion is allowed to pass through each through hole 115a to 115d. The length of the columnar contact portions 123a to 123c (length of the release member 120 in the pressing direction) is formed longer than a thickness (depth) of each corresponding through hole 115a to 115c. Thereby, distal ends of the contact portions 123a to 123c having passed through the through holes 115a to 115c are allowed to come to contact with the IOL 2. Further, when the release member 120 is entirely pressed against the restriction member 110 and then the release member 120 is arranged in parallel with a side surface of the body 30, the IOL 2 is retained horizontally on the axis L by the distal ends of the contact portions 123a to 123c. In other words, after the release member 120 is entirely pressed, the distal ends of the contact portions 123a to 123c form a setting surface 123e for horizontally placing the IOL 2 on the axis L. In the figure, the setting surface 123e is illustrated as diagonally shaded area.

The contact portions 123d (release portion) of columnar shape are formed longer than the contact portions 123a to 123c, but not long enough to contact with the end portions 113b in the storage state. The contact portions 123d lift the end portions 113b before the contact portions 123a to 123c come to contact with the IOL 2 to release restriction of the IOL 2. Therefore, when the IOL 2 passes the end portions 113b, the IOL 2 can be moved onto the axis L without contacting the end portions 113b. Further, not-shown wall surfaces (inner walls) of the contact portions 123d having passed the through holes 115d are formed along the peripheral edge 2c of the optical part 2a placed on the stage 111a. Thereby, the wall surfaces (inner walls) of the contact portions 123d serves as guiding portions, and the IOL 2 is moved onto the axis L along the wall surfaces of the contact portions 123d. Thus, the IOL 2 is prevented from misalignment in the horizontal direction when the IOL 2 is moved onto the axis L.

Since the length of each contact portion 123a to 123c is formed longer than the thickness (depth) of the corresponding through holes 115a to 115c, the setting surface (distal ends) 123e is positioned closer to the axis L than the base 111 of the restriction member 110 when the release operation using the release member 120 is completed. As a result, a space s is formed between the IOL 2 (back side surface) supported by the setting surface 123e and the base 111 (see FIG. 5C). In the space s, a viscoelastic substance to be used in folding the IOL 2 is filled. The viscoelastic substance is easily applied on the IOL 2 and the friction is reduced, so that the folding operation of the IOL 2 can be smoothly started.

The setting surface 123e is made up of at least one of the contact portions 123a to 123c and has an enough length (area) to horizontally place the IOL 2 on the axis L. Herein, the setting surface 123e is made up of the contact portions 123b and 123c. Further, the length of the contact portion 123a is formed shorter than the length of the contact portions 123b and 123c. By this configuration, when the IOL 2 is folded by the plunger 40, a center portion of the optical part 2a is out of contact with the contact portion 123a, reducing the load such as friction on the optical part 2a during folding of the IOL 2. Further, the contact portion 123a is formed shorter than the contact portions 123b and 123c, and thereby the center portion of the optical part 2a is pressed toward the axis L by the contact portion 123a at the ending of pressing the release member 120 against the restriction member 110. In this way, even when the IOL 2 remains sticking to the stage 111a, that sticking can be released. By the above mentioned operation, the whole IOL 2 is preferably placed on the setting surface 123e. Incidentally, it is preferable that a distal end (contact surface) of the contact portion 123a has a wide area. That is because the IOL 2 can be reliably pressed onto the axis L with the wide contact portion 123a.

When the IOL 2 is placed on the setting surface 123e (on the axis L), the wall surfaces of the contact portions 123d are arranged along the edge of the optical part 2a. Thereby, the wall surfaces of the contact portions 123d also serves as a misalignment prevention mechanism when the IOL 2 placed on the setting surface 123e is moved toward the front end 11 by pressing of the plunger 40.

Each contact portion 123d may have a length long enough to release the restriction by the end portions 113b before the IOL 2 passes through the end portions 113b. In other words, in accordance with the configuration of the injector 1, the length of each contact portion 123a to 123d may be equal.

In the present embodiment, the contact portion 123b corresponding to the support part 2b at the rear side is inclined, and the height is gradually increased from the centering portion 124 to the contact portion 123c. Therefore, when the IOL 2 is folded by the plunger 40, the support part 2b at the rear side is lifted along the slant surface. Further, the tip portion 44 is further easy to be lifted by the slant surface formed on the lower side of the tip portion 44 of the plunger 40. Thereby, the support part 2b retained by the tip portion 44 can be smoothly tucked onto the optical part 2a. After the tip portion 44 of the plunger 40 passed through the centering portion 124, the plunger 40 is moved onto the axis L. Thus, the tucked optical part 2a of the IOL 2 is preferably pushed by the tip portion 44.

On the other hand, at a distal end of the contact portion 123b corresponding to the support part 2b at the front side, protrusions 126a and 126b are provided for holding the IOL 2 from being pressed toward the front end 11 when the support part 2b at the rear side is tucked. In the present embodiment, the protrusions 126a and 126b are provided on left and right sides with respect to the axis L (slightly) closer to the front end 11 than the peripheral edge 2c of the optical part 2a. The protrusions 126a and 126b each have a shape and a size (heights) such that the protrusions 126a and 126b restrain movement of the optical part 2a in response to the pressing force pressing only the support part 2b at the rear side by the tip portion 44 and allow the optical part 2a to pass when the pressing force large enough to press both the rear support part 2b and the optical part 2a. The protrusions 126a and 126b preferably have smooth curved surfaces for restraining load to be applied to the optical part 2a when passing. By the protrusions 126a and 126b, tucking of the IOL 2 is reliably conducted. The whole IOL 2 is pressed after the tucking operation is completed, and the folding operation is properly started.

Further in the present embodiment, rotation of the IOL 2 during tucking can be prevented by the two protrusions 126a and 126b. Furthermore, inner sides of the protrusions 126a and 126b where the optical part 2a is to pass are formed as inclined surfaces, and thereby the optical part 2a is easily guided to a midpoint between the protrusions 126a and 126b when the optical part 2a goes through between the protrusions 126a and 126b. As a result, folding of the IOL 2 is easily started.

In conventional arts, the IOL 2 pushed by the release member 120 is temporarily separated from the release member and deformed and then moved onto the axis L. Thus, there is a possibility that the IOL 2 could be inclined in an unintended manner or be folded while moving onto the axis L. On the other hand, in the present invention, the released IOL 2 is correctly (horizontally) placed on the setting surface 123e on the axis L without being separated from the release member 120.

The contact portions 123a to 123c of the release member 120 become the setting surface 123e for the IOL 2. Therefore, when the release member 120 is entirely pressed against the body 30, the folding operation of the IOL 2 by the plunger 40 can be started without detaching the release member 120 from the body 30. Further, since there is no clearance is created between the IOL 2 and the setting surface 123e, the IOL 2 is placed on the setting surface 123e with no clearance. Thereby, the plunger 40 does not slip under (run onto) the optical part 2a and is properly pressed, thus the IOL 2 being properly folded.

The IOL 2 retained by the restriction member 110 is successively pressed in one direction from the rear end side to the front end 11 side by the release member 120. Specifically, each contact portion 123a to 123c successively comes to contact with the IOL 2 retained obliquely on the base 111 from the rear end side to the front end side. Therefore, according to the pressing amount of the release member 120, a contact surface area (pressing amount) of the contact portion 123 to the IOL 2 is increased in one direction from the rear support part 2b to the front support part 2b. Thus, even when the IOL 2 remains sticking to the base 111 during storage, the IOL 2 can be unstuck in one direction. As a result, the IOL 2 can be moved onto the axis L without being subjected to unnecessary load.

After the IOL 2 is placed on the setting base 31 on the axis L by the restriction release operation by the release member 120 as mentioned above, the IOL 2 is allowed to be injected in an eye.

The centering portion 124 is formed on its upper surface with a recess 124a having a shape substantially conforming to an outer shape of the plunger 40. When the release member 120 is entirely pressed, the recess 124a is aligned with the position where the plunger 40 passes on the axis L, and the recess 124a is used as a pushing mechanism of the plunger 40. In the present embodiment, on the distal end (upper surface) of the contact portion 123b corresponding to the support part 2b, a groove 125 is formed with an almost equal shape with an outer shape of the push rod 43 of the plunger 40 and extending in a back and forth direction (axial direction) of the IOL 2. This groove 125 is also used as the pushing mechanism of the plunger 40.

According to the above mentioned configuration, the IOL 2 is stored in a state that no stress is applied by the plurality of restriction parts 112 and 113 of the restriction member 110. On the other hand, the storage state of the IOL 2 is easily released by the pressing force pressing the release member 120.

Since the setting surface 123e is made up of the release member 120, operator can shortly start the folding operation of the IOL 2 without detaching the release member 120 after the restriction of the IOL 2 is released. Further, while the IOL 2 is moved from outside the axis onto the axis, the IOL 2 can be maintained in a horizontal state, and thereby the released IOL 2 is stably placed in the injector 1. Furthermore, there is no clearance between the released IOL 2 and the setting surface 123e, so that it is preventable to have problems caused by the plunger 40 running onto the optical part 2a or slipping under the optical part 2a while the IOL 2 is folded.

By utilizing the contact between the IOL 2 and the setting surface 123e, the operation of tucking a part of the rear support part 2b onto the optical part 2a can be easily conducted. In conventional arts, in order to smoothly fold the IOL inside the injection part, the IOL is mostly placed in a state that the viscoelastic substance has been applied on the setting surface 123e in advance. However, the IOL placed on the viscoelastic substance is in an unstable state, and the tucking operation becomes difficult. In response to this, in the present disclosure, the IOL is retained on the setting surface 123e during tucking with a predetermined friction force generated between the setting surface 123e and the IOL 2. When the IOL 2 is folded, the pressing force equal to or larger than the friction force of the setting surface 123e is applied by the plunger 40 so that the retention of the IOL 2 is easily released.

For example, the setting surface 123e formed as a mirror surface is formed to only come to contact with the peripheral edge of the optical part 2a. Other than this configuration, a surface state and a shape of the setting surface 123e are determined according to a combination of the IOL 2 and a material forming the setting surface 123e. Further, when the IOL 2 is retained on the setting surface 123e during tucking, the configuration of the injector 1 may be simpler by omitting the protrusions 126a and 126b for preventing rotation of the IOL 2.

In the present embodiment, the released IOL 2 is placed on the setting surface 123e, and then the space s in which the viscoelastic substance is allowed to be injected is created between the stage 111a and the lower side surface of the optical part 2a. In a state that the IOL 2 is retained on the setting surface 123e, when the viscoelastic substance is injected in the space s, the viscoelastic substance is easily applied on the lower side of the optical part 2a. Especially, in the present embodiment, the setting surface 123e is configured such that the surface 123e only comes to contact with the peripheral edge of the IOL 2, and thereby the viscoelastic substance is properly applied on the center portion of the lower side of the optical part 2a located in the space s. Thereby, the friction force generated when the IOL 2 is folded inside the injection part 10 is reduced by the viscoelastic substance. Thus, the IOL 2 is smoothly moved toward the front end 11.

Figure 5A:
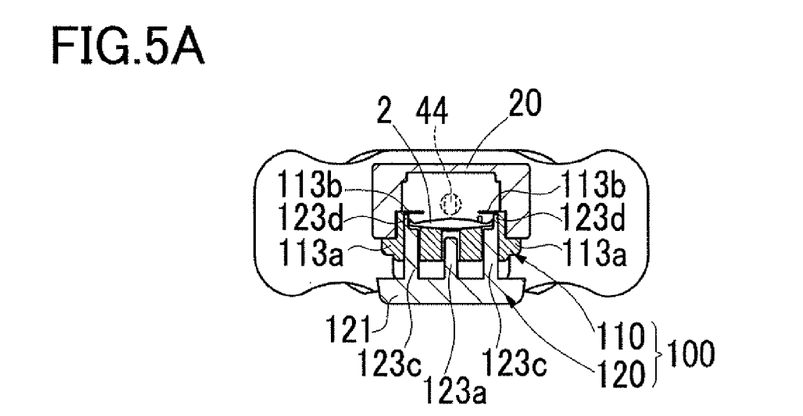
FIG. 5A is an explanatory view showing an operation of releasing restriction of the IOL.
Figure 5B:
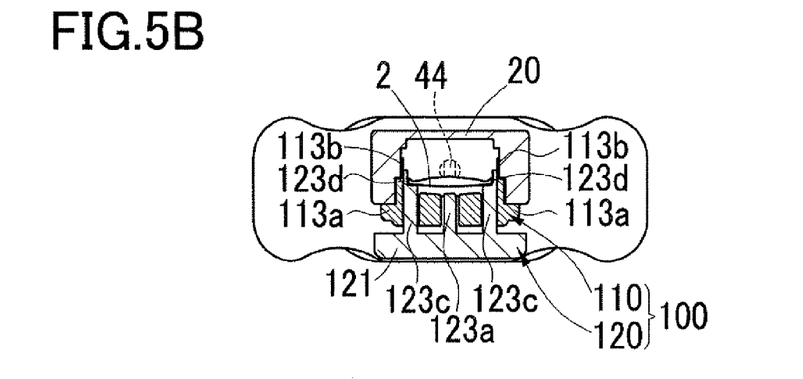
FIG. 5B is another explanatory view showing the operation of releasing the restriction of the IOL.
Figure 5C:
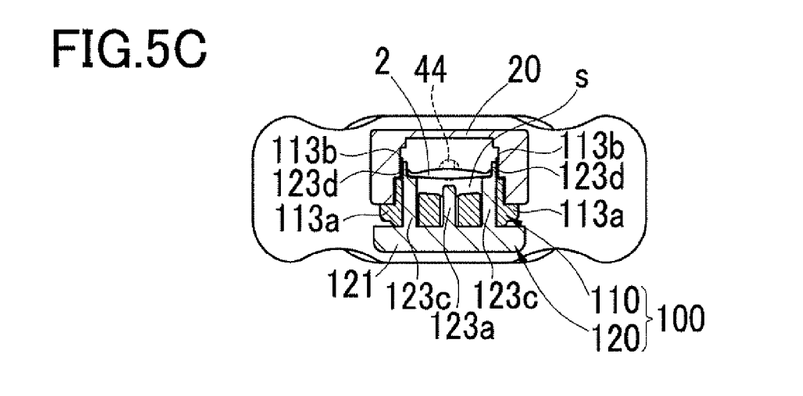
FIG. 5C is another explanatory view showing the operation of releasing the restriction of the IOL.
Figure 6A:
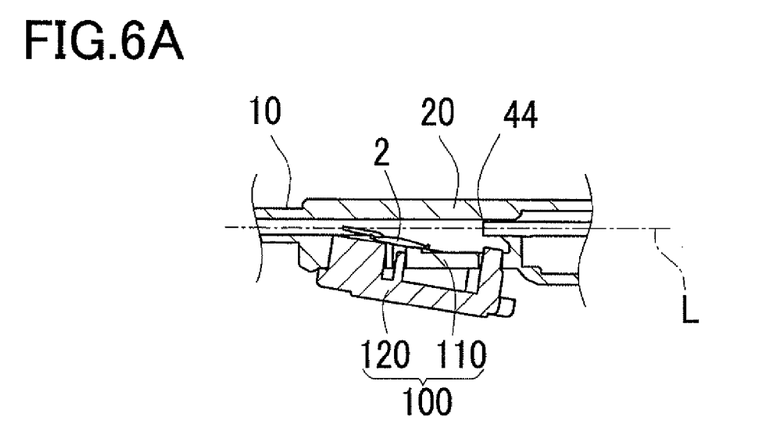
FIG. 6A is an enlarged sectional view of an injection part and its surroundings for injecting the IOL.
Figure 6B:
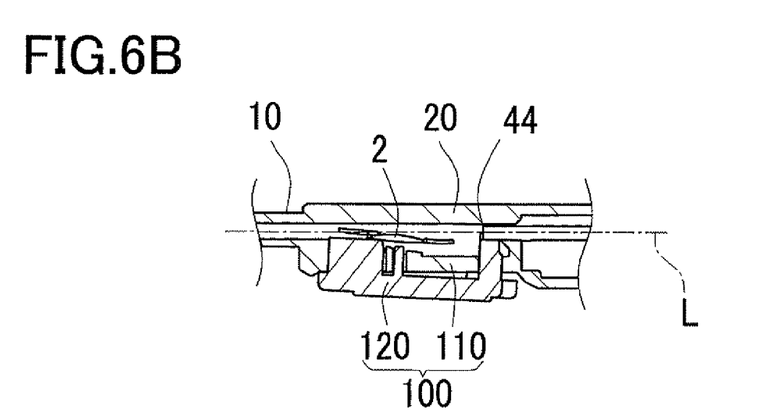
FIG. 6B is another enlarged sectional view of the injection part and its surroundings for injecting the IOL.
Figure 6C:
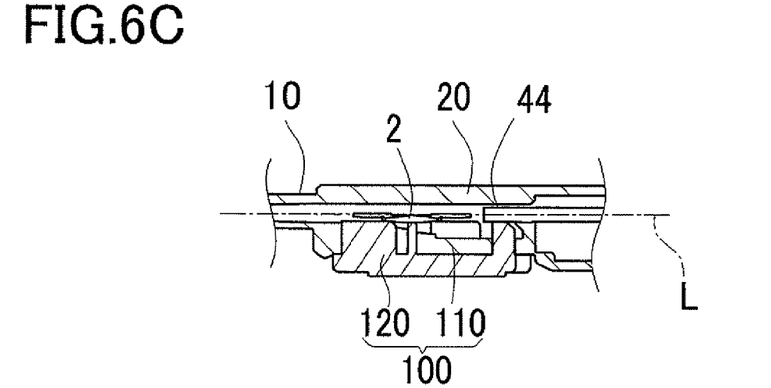
FIG. 6C is another enlarged sectional view of the injection part and its surroundings for injecting the IOL.

Next, a pushing operation of the IOL 2 by use of the injector 1 having the above-mentioned configuration will be explained. FIGS. 5A to 5C and FIGS. 6A to 6C are explanatory views showing the operation that the IOL 2 is shifted from a restriction state (outside the axis L) to a use state (on the axis L). FIGS. 5A to 5C are sectional diagrams of the injector 1 taken along a line A-A (see FIGS. 2A and 2B) and seen from the front end 11 side. FIGS. 6A to 6C are sectional diagrams of the injector 1 shown in FIGS. 2A and 2B, showing enlarged views of the storage part 100 and its surroundings. In FIGS. 5A to 5C and FIGS. 6A to 6C, reference signs of some components are omitted.

FIGS. 5A and 6A show a state that the IOL 2 is stored in the storage part 100 outside the axis L. The IOL 2 is retained obliquely relative to the axis L by the restriction member 110. Further, the IOL 2 is retained without being subjected to any stress from the restriction parts 112 and 113. The restriction parts 112 and 113 (the columnar portions 113a) are not deformed by the weight and oscillation of the IOL 2. Specifically, even when the force due to the oscillation of the IOL 2 and others is applied to the restriction parts 112 and 113 or when the injector 1 is placed downward (the state that the storage part 100 is positioned above the body 30) and the weight of the IOL 2 acts on the columnar portions 113a, the retention of the IOL 2 is not released by deformation of the restriction parts 112 and 113 (columnar portions 113a).

When an operator pushes the release member 120 (pressing part 121) for releasing the restriction of the IOL 2 by the storage part 100, as shown in FIGS. 5B and 6B, the release member 120 rotates about the restriction member 110 to come closer to the axis L. In other words, the release member 120 rotates about its not-shown rotational axis to bring the other end (rear end) closer to the restriction member 110.

Thus, the contact portions 123a to 123d pass each through hole 115a to 115d (omitted with the reference signs) of the storage part 100. The contact portions 123d having passed the through holes 115d come to contact with the end portions 113b. The pressing part 121 is further pressed, and then the end portions 113b are gradually deformed toward outside at the connecting points with the columnar portions 113a by the pressure applied by the contact portions 123*d*. The pressing part 121 is further pressed and then the contact portions 123*a* to 123*c* pass through holes 115*a* to 115*c* and come to contact with the IOL 2. At this time, the IOL 2 is moved onto the axis L as guided by the wall surfaces of the contact portions 123*d* that have passed the through holes 115*d*.

Since the IOL 2 passes positions where the end portions 113*b* are used to be located, the end portions 113*b* having been deformed toward outside by the contact portions 123*d*, the IOL 2 can be moved onto the axis L without contacting the end portions 113*b*. Namely, problems such as breakage due to unnecessary load applied to the peripheral edge of the optical part 2*a* can be prevented. Further, the IOL 2 (optical part 2*a*) is guided by the wall surfaces of the contact portions 123*d* when moved onto the axis L, so that an inclination in the horizontal direction can be restrained.

As shown in FIGS. 5C and 6C, when the release member 120 is entirely pressed against the restriction member 110 (body 30), the IOL 2 is placed horizontally on the setting surface 123*e* (contact portions 123*b* and 123*c*) without being folded. At this time, there is no clearance created between the IOL 2 and the setting surface 123*e*. Therefore, when the IOL 2 is pushed by the plunger 40, scratches on the IOL 2 is prevented, the scratches being caused by the tip portion 44 running onto the optical part 2*a* or slipping under the optical part 2*a*. The groove 125 formed on the contact portions 123*b* having passed the through holes 115*b* and the centering portion 124 having passed the through hole 115*e* constitute a centering mechanism for guiding the back and forth movement of the plunger 40.

As explained above, the release member 120 is used as the centering mechanism for pushing the IOL 2 toward the front end 11, and thereby the folding operation of the IOL 2 can be started without detaching the release member 120.

While the IOL 2 is placed on the setting surface 123*e*, an operator rotates the injector 1 to be aligned with an orientation of the bevel of the front end 11. Then, a known viscoelastic substance is injected in the injection part 10 from a not-shown opening or the front end 11. The viscoelastic substance is injected in the space s formed between the stage 111*a* and the lower side surface of the optical part 2*a*. Herein, the lower side of the IOL 2 is placed on the setting surface 123*e*, and therefore the operator can easily check the state of the IOL 2 on the setting surface 123*e* from the body 30 side facing the release member 120.

When the operator pushes the press part 41, the plunger 40 moves in the axial direction along the recess 124*a* and the groove 125 as the centering mechanism. By this centering mechanism, the back and forth movement of the plunger 40 is stabilized and thereby the folding of the IOL 2 can be reliably conducted.

First, the support part 2*b* at the rear side is pushed at its folding point by the tip portion 44 of the plunger 40 and then tucked. A part of the optical part 2*a* is retained by the setting surface 123*e* at this time, and therefore the tucking operation is reliably made. When the press part 41 is further pressed, the tip portion 44 comes to contact with the peripheral edge (edge) of the optical part 2*a*. Then, the optical part 2*a* gets over the protrusions 126*a* and 126*b* by the pressing force applied to the optical part 2*a* to move toward the front end 11, and then the optical part 2*a* is gradually folded (rounded) along the inner wall of the injection part 10.

At this time, in the present embodiment, the lower side of the optical part 2*a* being in contact with the setting surface 123*e* is folded along the inner wall of the injector 1. The press part 41 is further pressed and the IOL 2 is folded and injected in an eye from the front end 11. Then, the IOL 2 is gradually unfolded in a capsular. The pair of the support parts 2*b* are arranged along the capsular, and thereby the optical part 2*a* is retained by the stress applied in the eye.

The above explanation has been made with an injector constituted in such a way that an injector body and an IOL storage part are integrally formed (an injector of preset type or preloaded type), but the injector is not limited to this one. For example, the present invention may be applied to an injector including an injector body and an IOL storage part which are formed separately. This configuration makes it easy to switch the restriction state and the use state of the IOL. Alternatively, the present invention may be applied to an injector (of semi-preset type or semi-preloaded type) constituted in a manner that an IOL storage part constitutes a part of an injector body (the IOL storage part forms a part of an inner wall of an injection part of the injector body).

The present invention is not limited to the above configuration. In the above examples, the IOL 2 in the storage state is placed obliquely relative to the axis L. Alternatively, the IOL 2 may be retained outside the axis L so that the IOL 2 is placed in parallel with the axis L in the storage state. In this case, the restriction of the IOL 2 is released only by pushing the release member 120 and the release member 120 can be used as the setting surface 123*e* without being detached, and thereby the IOL 2 is preferably placed on the setting surface 123*e*, so that the pushing operation of the IOL 2 in the use state is preferably conducted.

The invention claimed is:

1. An intraocular lens injection instrument for injecting an intraocular lens (IOL) into a patient's eye, the intraocular lens injection instrument comprising:

a cylinder body part;

an injection part that is formed at an end of the cylinder body part, the injection part having an inner wall that folds the IOL, and a front end that injects the IOL folded along the inner wall into an eye, the IOL being a soft IOL;

a push member that pushes the IOL toward the front end of the injection part, the push member being movable back and forth along an axis extending from the front end of the injection part to a rear end of the intraocular lens injection instrument;

a restriction member attached to the cylinder body part, the restriction member being configured to restrict movement of the IOL when it is placed outside of the axis, the restriction member including a pair of elements formed to face each other, the pair of elements restricting movement of the IOL; and a release member that is provided below the IOL when the IOL is placed outside of the axis, the release member including a contact portion and a columnar release part, the release member being configured to (i) release restriction of the movement of the IOL restricted by the restriction member, and (ii) push up the IOL onto the axis, wherein at least one of the pair elements of the restriction member is a deformable restriction part that restricts movement of the IOL when the IOL is moved by the release member in a pushing direction, the deformable restriction part including (i) an end portion extending inward from a periphery of a lens surface by a predetermined amount to support the lens surface on an upper side of the IOL, and (ii) a columnar portion for supporting the end portion;

the columnar release part of the release member is formed in a position so as to be configured to contact the end portion of the deformable restriction part and deform the end portion, with respect to the columnar portion, in a pushing direction to release the restriction of the IOL;

when the end portion of the deformable restriction part is pressed by the columnar release part, the end portion is deformed in the pushing direction so that the IOL moves onto the axis without contacting the deformable restriction part; and when the restriction by the restriction member is released, the contact portion of the release member is brought into contact with the IOL, the contact portion having a setting surface that is brought into contact with the IOL when the IOL is pushed up and placed on the axis.

2. The intraocular lens injection instrument according to claim 1, wherein the end portion is a protruding component that is brought into contact with the lens surface, and has a thickness deformable in a moving direction of the IOL when the end portion is pressed by the release part.

3. The intraocular lens injection instrument according to claim 2, wherein the restriction member includes a through hole formed between the columnar portion and a peripheral edge of an optical part of the IOL, when the IOL is placed in the intraocular lens injection instrument, and the release part is formed in a position of the release member in which the release part is allowed to pass through the through hole.

4. The intraocular lens injection instrument according to claim 3, wherein the release part includes a guide portion for preventing misalignment of the IOL when the IOL is moved onto the axis, the guide portion being a wall surface formed in a position along an outer periphery of the IOL, when the IOL is placed in the intraocular lens injection instrument.

5. The intraocular lens injection instrument according to claim 4, wherein the release member includes a centering portion that guides the push member to move in an axial direction in a state that the IOL is released from the restriction.

* * * * *